United States Patent [19]

Nardo

[11] Patent Number: 5,047,129
[45] Date of Patent: Sep. 10, 1991

[54] UNIT FOR THE TREATMENT OF ELECTROPHORETIC STRIPS

[76] Inventor: Pietro Nardo, Viale Buffoli, 21, 20095 Cusano Milanino (Milano), Italy

[21] Appl. No.: 459,689

[22] Filed: Jan. 2, 1990

[30] Foreign Application Priority Data

Jan. 16, 1989 [IT] Italy ................... 19099 A/89

[51] Int. Cl.⁵ ........................... G01N 27/26
[52] U.S. Cl. ..................... 204/182.8; 204/299 R; 137/386; 137/391
[58] Field of Search ......... 204/180.1, 182.8, 299 R; 137/386, 391

[56] References Cited

U.S. PATENT DOCUMENTS

| | | | |
|---|---|---|---|
| 3,920,550 | 11/1975 | Farrell, Jr. et al. | 210/86 |
| 4,073,663 | 2/1978 | Lundgren | 134/30 |
| 4,360,418 | 11/1982 | Golias | 204/182.8 |

FOREIGN PATENT DOCUMENTS 0209866 1/1987 European Pat. Off. .
22221B88 5/1990 Italy .

Primary Examiner—T. Tung
Assistant Examiner—David G. Ryser
Attorney, Agent, or Firm—Griffin Branigan & Butler

[57] ABSTRACT

A unit for the treatment of electrophoretic strips mounted on a frame comprises at least one pair of basins (10a, 10b) and a feed, forced circulation and emptying circuit comprising as many tanks (23, 24) as there are different treatment liquids, a single tank (25) containing a rinsing liquid, a single tank (26) for discharging the treatment liquids and at least one pair of pumps (29, 30).

19 Claims, 2 Drawing Sheets

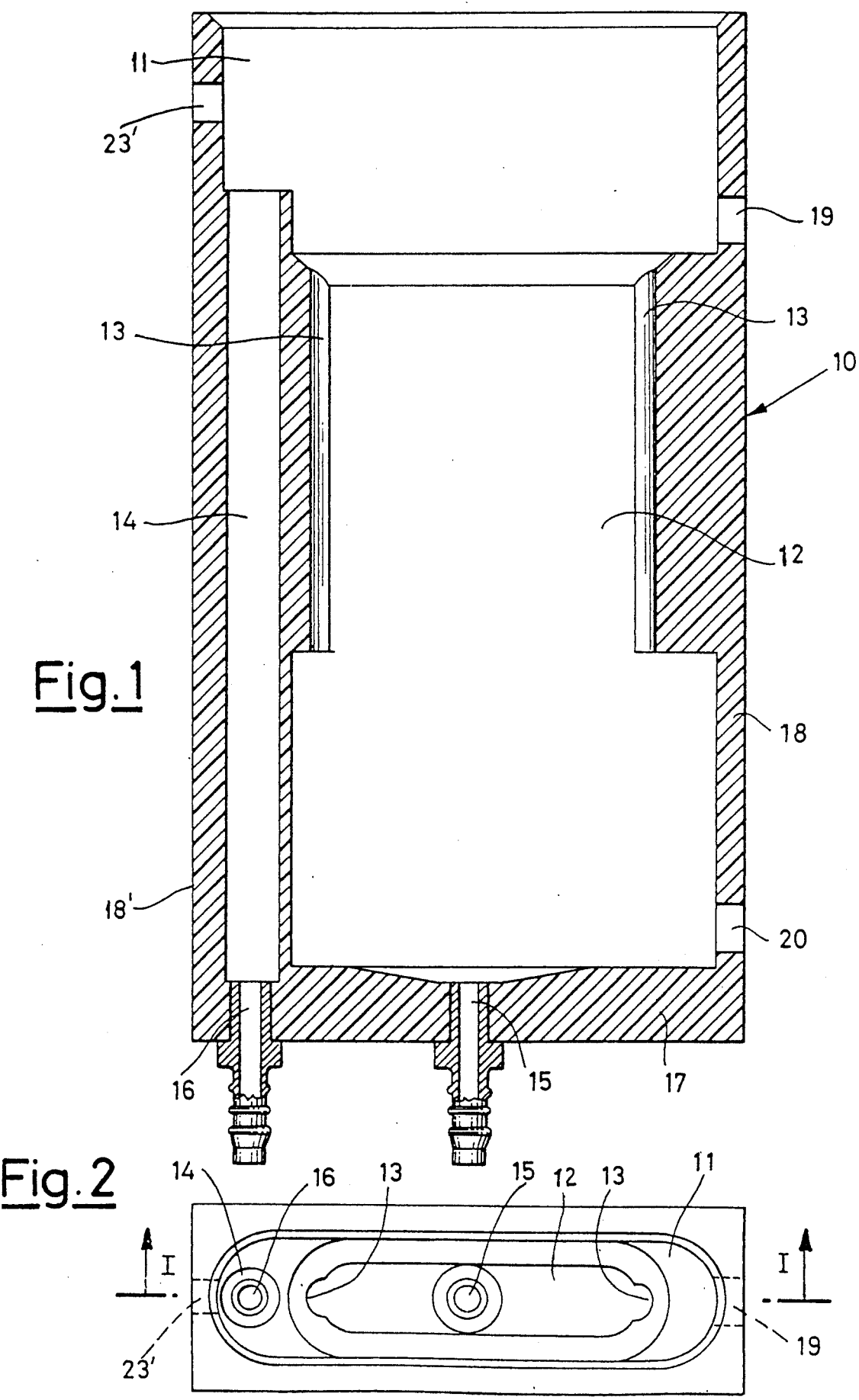

UNIT FOR THE TREATMENT OF ELECTROPHORETIC STRIPS

BACKGROUND

1. Field of the Invention

The present invention relates to a unit for the treatment of electrophoretic strips. The unit comprises a plurality of basins for holding liquid substances suitable for the treatment of blood samples, deposited on said strips for the determination of serum proteins, hemoglobin, lipids and such like.

2. Prior Art and Other Considerations

Units for the treatment of electrophoretic strips are well known to persons skilled in the art.

A type of unit currently adopted with more than satisfactory results has a structure which, in brief, comprises, in combination: a succession of basins placed side by side wherein the electrophoretic strips, each mounted on a special frame, are immersed into appropriate treatment baths, and means of transport for moving the strips from one to the other of said basins and for their immersion into said baths.

Such a unit is described and illustrated in the Italian Industrial Patent Application No. 21639 A/85, filed on July 19, 1985, in the name of the same Applicant. A particular type of supporting frame for electrophoretic strips is, on the other hand, described and illustrated in the Italian Utility Model Application No. 22221 B/88, filed on Nov. 29, 1988, in the name of the same Applicant.

For further information on this, please see the above Applications.

The general object of the present invention is to accomplish a unit having small side-by-side tanks wherein at least two basins are connected to a feed, forced circulation and emptying circuit so that the electrophoretic strip positioned in each basin—preferably on a frame of the type described in Application No. 22.221 B/88—may be treated in succession with different baths. Another object of the present invention is that said feed, emptying and forced circulation circuit may serve both basins with a minimum number of components, in that some of them can be common.

The objects described above are accomplished, according to the present invention, by a unit for the treatment of electrophoretic strips mounted on a frame characterized in that it comprises, in combination: at least one pair of basins and a feed, forced circulation and emptying circuit comprising as many tanks as there are different treatment liquids, a single tank containing a rinsing liquid, a single tank for discharging the treatment liquids and at least one pair of pumps drawing the treatment liquids from their respective tanks to feed them to the basins through draw lines controlled by means of solenoid valves arranged upstream from the pumps, said pumps being also connected to the rinsing liquid tank in order to draw it alternatively into one or the other basin through draw lines controlled by solenoid valves also arranged upstream from the pumps, the circuit comprising in addition solenoid valves whereby it is possible to actuate a forced circulation of the rinsing liquid in each basin, both basins being also suitable for discharging the treatment liquids into the same tank both through an overflow conduit, and by means of said pumps along a line controlled by solenoid valves.

Preferably each of the basins has a central compartment and a vertical conduit, which is obtained to one side of said central compartment, which are suitable for being connected to said feed, forced circulation and emptying circuit, in addition, each basin, in the proximity of the top of each basin itself and at a point above the mouth of said vertical conduit, has an opening for discharging any overflow, there being also provided in said central compartment means for the positive positioning of said frame.

Preferably said means for positioning the frame are constituted by a pair of opposed guideways.

Even more preferably said opposed guideways are inclined towards the centre of the basin, so that said central compartment has a greater width at its lower end.

In addition, each basin can be provided with an upper and with a lower lateral opening suitable for receiving level detecting elements. The bottom of each basin is preferably provided with a fitting for connecting the central compartment and the vertical conduit, respectively, to said feed, forced circulation and emptying circuit of said basin.

The pumps used in the unit according to the present invention are preferably of the gear type operating in both directions. In turn both the filling and the emptying of each basin is preferably controlled both by means of level detecting elements and by timer devices.

BRIEF DESCRIPTION OF THE DRAWINGS

The structural and functional features of the unit according to the present invention shall be more clearly illustrated by the following description, with reference to the enclosed block diagrams, which show an example of a unit according to the present invention wherein a pair of basins is combined with a feed, forced circulation and emptying, or discharging, circuit, of the treatment liquids. In the drawings:

FIG. 1 is a vertical cross-sectional view taken along the line I—I of FIG. 2 illustrating a preferred type of basin according to the invention;

FIG. 2 is a plan view of the basin of FIG. 1; and

DETAILED DESCRIPTION OF THE DRAWINGS

Figure 3:
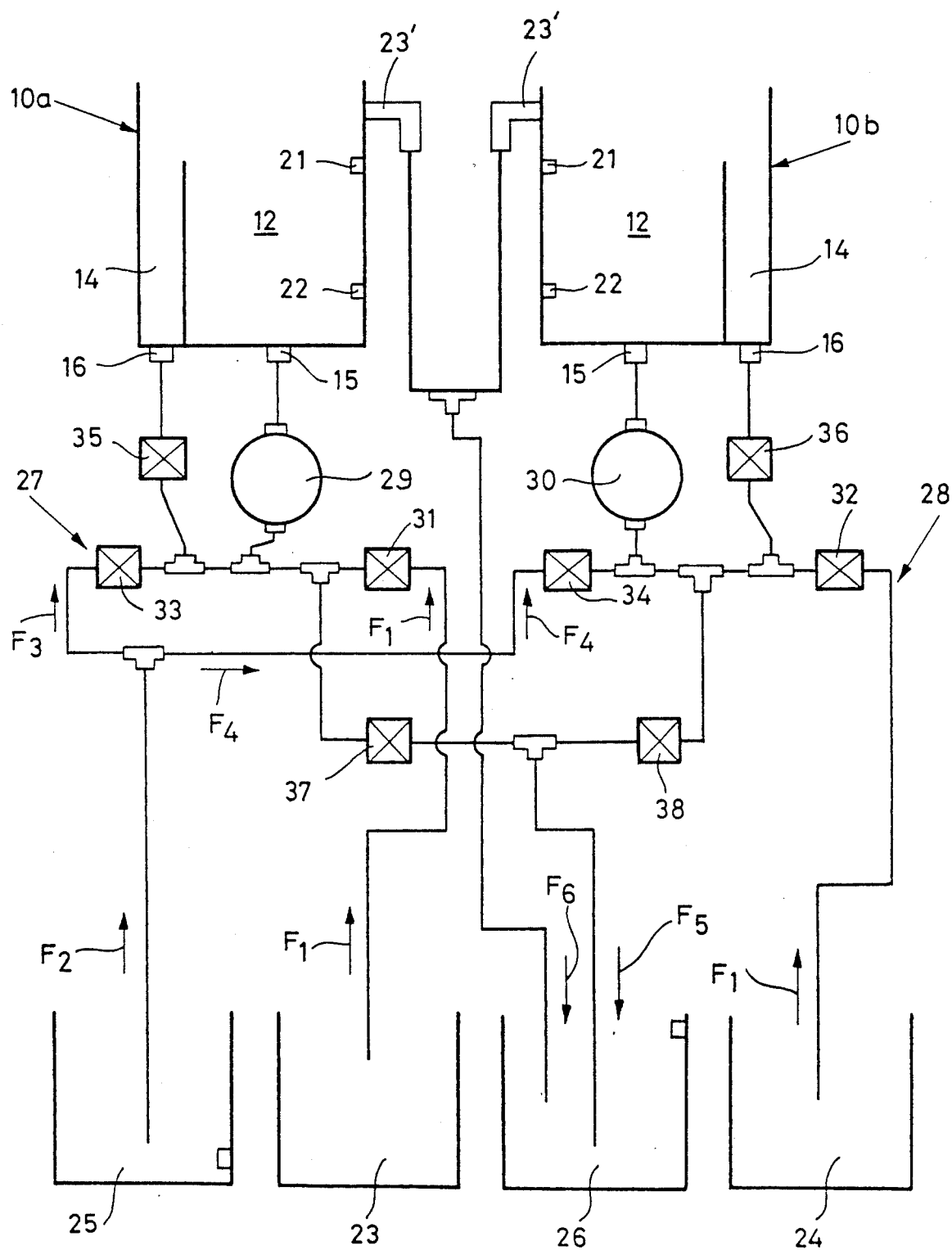
FIG. 3 is a diagram illustrating a unit of the invention which comprises one pair of the basins shown in FIGS. 1 and 2.

If we first of all refer to FIGS. 1 and 2 of the drawings, each basin 10, preferred in the accomplishment of the unit of the invention (FIG. 3), has the shape of a parallelepiped and, through a flared mouth 11 in the top, is suitable for receiving a frame (not shown) holding an electrophoretic strip.

The basin 10 can be accomplished by machining one or more pieces of a plastic material inert to the treatment liquids and which, moreover, has surface features such as to prevent as much as possible undesired stagnations of liquid.

As can be clearly seen from FIGS. 1 and 2 of the drawings, the basin 10 has a general structure which, in combination, comprises: a central compartment 12, which is provided with opposed lateral guideways 13 for receiving the above frame by insertion, and a vertical conduit 14 which is obtained to one side of said central compartment 12.

Compartment 12 and conduit 14, by means of respective fittings 15, 16 provided in the bottom 17 of basin 10, may be connected (as shall be explained in detail later with reference to FIG. 3) to a feed, forced circulation and emptying and discharging circuit of the treatment and rinsing liquids.

In addition, basin 10, on the side wall 18 opposite to conduit 14, has a pair of openings 19, 20 for receiving sensor elements 21, 22 (FIG. 3) able to detect the maximum and minimum levels, respectively, attained by the liquid inside the basin.

On the other side wall 18', above conduit 14, basin 10 lastly also has an opening 23' for discharging any overflow.

A basin 10, illustrated as a non-limiting example in FIGS. 1 and 2 of the drawings, may be used to advantage for treating, with special liquids, blood samples carried by electrophoretic strips supported on frames which are introduced vertically, with their longer side, into compartment 12 guided and positioned in a positive manner by means of the lateral guideways 13.

It should be noted that, as can be clearly seen from FIG. 1 of the drawings, that the lateral guideways 13 are inclined inwards towards the central symmetry axis of basin 10 (so that compartment 12 has a greater width at its lower end) so as to avoid that the strip-supporting frame may interfere with the minimum-level sensor 22.

Feeding, discharging or emptying, and the forced circulation of the treatment and rinsing liquids inside compartment 12 of a plurality of basins combined to form a unit for the treatment of electrophoretic strips may be governed in a preset manner; to this end the circuit shown in FIG. 3 of the drawings is provided.

Said circuit comprises four tanks 23, 24, 25 and 26. Tanks 23 and 24 may contain dyeing baths for highlighting serum proteins and lipids, respectively. The tank 25 contains a rinsing bath, while treatment liquids are discharged into tank 26. Accordingly, tank 23 and 24 are also known as liquid treatment or treatment tanks; tank 25 is also known as a rinsing tank; and, tank 26 is also known as a discharge tank.

Vessels 10a and 10b are operationally connected to the tanks 23, 24, 25 and 26 by means of a circuit formed by two parts 27 and 28 which are of a substantially specular structure.

That said, said circuit comprises a pair of pumps 29, 30, say of the gear type which can operate in both directions, which draw in the dyeing substances from respective tanks 23 and 24 to feed them along the direction of arrows F1 to basins 10a and 10b. The passage of the dyeing substances through the draw lines is controlled by means of treatment solenoid valves 31, 32 arranged upstream from pumps 29, 30.

The two pumps 29, 30 draw in the rinsing liquid from the same tank 25, along the direction of arrow F2, to feed it either to basin 10a, along the direction of arrow F3, or to basin 10b, along the direction of arrow F4. The feeding of the rinsing liquid in the directions of arrows F3 and F4 is controlled by respective rinsing solenoid valves 33, 34, which are also arranged upstream from pumps 29, 30, while circulation solenoid valves 35, 36, as shall be explained later, allow the execution of a forced circulation of the rinsing liquid between 12 and 14.

Lastly, both basins 10a and 10b may discharge the treatment baths into the same tank 26, both by means of pumps 29, 30, along the direction of arrow F5, and through overflow 23', along the direction of arrow F6. Discharge of basins 10a and 10b, through pumps 29, 30 is controlled by means of solenoid valves 37, 38.

By combining two basins, having the functional characteristics of that illustrated as a non-limiting example in FIGS. 1 and 2, with the circuit described above, a unit may be accomplished according to the present invention which has the following operational cycle.

A suitable bath dyeing the serum proteins, taken from tank 23, is fed into basin 10a by operating the pump 29 with solenoid valve 31 open and solenoid valves 33, 35 and 37 closed.

The maximum level sensor 21 stops pump 29 when the preset level of the dyeing liquid inside basin 12 has been reached. On this matter it should be pointed out that, if sensor 21 is not triggered, a timer is provided which stops pump 29. If neither the level sensor 21 nor this timer are triggered, the dyeing substance is discharged into tank 26 through overflow 23.

After the dyeing liquid has remained for a time sufficient for the treatment of the blood sample (say, 5 minutes), pump 29 is operated in reverse and the dyeing liquid is thus discharged into tank 26 through the open solenoid valve 37, while solenoid valves 31 and 38 are closed.

If it is desired to recover the dyeing liquid in order to recycle it, the same can, on the other hand, be made to return to tank 23 by opening solenoid valve 31, with solenoid valve 37 closed.

So as to ensure the complete emptying of compartment 12, the minimum level sensor 22 is triggered to operate pump 29 for a further period, say, about 15 seconds, so as to ensure complete emptying of the circuit. If sensor 22 is not triggered, a timer will ensure the operation of pump 29 for the above period.

The dyeing stage of the electrophoretic strip is thus completed.

The rinsing stage is executed by withdrawing liquid from tank 25 by operating the pump 29 with solenoid valve 33 open, while solenoid valves 31, 35 and 37 are closed.

As soon as the maximum level sensor 21 is triggered, solenoid valve 33 is closed, while solenoid valve 35 is opened, keeping solenoid valves 31 and 37 closed.

The rinsing stage may thus be executed for the desired period of time, say, about 2-3 minutes, with the rinsing bath which is made to circulate forcibly by pump 29 in a closed circuit between 12 and 14.

To discharge the rinsing bath, proceed as described above for the dyeing liquid, reversing the direction of pump 29 and closing solenoid valves 31, 33, while opening solenoid valves 35 and 37.

The cycle described above with reference to basin 10a, for the dyeing of serum proteins, may be repeated in basin 10b, say, for the dyeing of lipids.

On this matter it should be pointed out that the particular structure of the circuit according to the present invention, in a unit comprising at least two basins, allows the utilization of a single tank 25 containing the rinsing bath and a single tank 26 for discharging the treatment baths with appreciable advantages in terms of both compactness and final cost of the unit.

There are thus attained the objects mentioned in the preamble to the description.

I claim:

1. A unit for the treatment of electrophoretic strips mounted on a frame characterized in that it comprises, in combination:

at least one pair of basins for receiving said frames; and, a feed, forced circulation and emptying circuit comprising:
- as many treatment liquid tanks as there are different treatment liquids;
- a single rinsing tank containing a rinsing liquid;
- a single discharge tank for discharging the treatment liquids; and,
- at least one pair of pumps, each of said pumps being connected to an associated one of said basins, each of said pumps also being connected by an associated treatment draw line to one of said treatment liquid tanks for drawing a treatment liquid from its tank into its associated basin, each of said pumps also being connected by a rinse draw line to said single rinsing tank in order to alternatively draw the rinsing liquid into said basins;
- a discharge line from each of said basins to said single discharge tank;
- a solenoid valve provided on each of said liquid treatment lines, said rinse line, and said discharge line for permitting a forced circulation of the rinsing liquid in each basin, both basins also being connected for discharging the treatment liquids into the same discharge tank both through an overflow conduit, and by means of said pumps along said discharge line controlled by solenoid valves.

2. A unit according to claim 1, characterized in that each basin has a central compartment and a vertical conduit, which is obtained to one side of said central compartment, said central compartment and said vertical conduit each being connected through fittings to lines included in said feed, forced circulation and emptying circuit, and that each basin, in the proximity of the top of each basin itself and at a point above the mouth of said vertical conduit, has an opening for discharging any overflow, there being also provided in said central compartment means for the positive positioning of said frame.

3. A unit according to claim 2, characterized in that said means for positioning the frames are constituted by a pair of opposed guideways.

4. A unit according to claim 3, characterized in that said opposed guideways are inclined towards the centre of the basin, so that said central compartment has a greater width at its lower end.

5. A unit according to claim 2, characterized in that each basin has side openings suitable for receiving level sensor elements.

6. A unit according to claim 2, characterized in that the bottom of each basin is provided with fittings for connecting the central compartment and the vertical conduit, respectively, to said feed, forced circulation and emptying circuit of said basin.

7. A unit according to claim 2, characterized in that each basin has a flared mouth at the top.

8. A unit according to claim 2, characterized in that each basin has the shape of a parallelepiped.

9. A unit according to claim 1, characterized in that said pumps are of the gear type operating in both directions.

10. A unit according to claim 1, characterized in that the filing and emptying of each basin is controlled both by level sensors and by timers, said level sensors being provided in said basins and connected to said timers, said timers in turn being connected to solenoid valves.

11. A unit according to claim 1, wherein each of said pumps is connected to a first fitting provided in its associated basin, wherein each basin has a second fitting connected to a circulation solenoid valve, and wherein:
- a first treatment solenoid valve is connected on a first treatment draw line between a first liquid treatment tank and a first pump;
- a first rinse solenoid valve is connected on said rinse draw line between said rinse basin and said first pump;
- a first discharge solenoid valve is connected on said discharge line between a first basin and said discharge tank;
- a first circulation solenoid valve is provided on a line which communicates with said discharge line;
- whereby rinse liquid from said rinsing tank is pumpable through said first rinse solenoid valve and through said first fitting into said first basin, and liquid in said first basin is discharged through said second fitting and through said circulation solenoid valve into said discharge line and through said discharge solenoid valve into said discharge tank.

12. A unit according to claim 11, wherein:
- a second rinse solenoid valve is connected on said rinse draw line between said rinse basin and said second pump;
- a second discharge solenoid valve is connected on said discharge line between a second basin and said discharge tank;
- a second circulation solenoid valve is provided on a line that terminates intermediate said second pump and said second rinse solenoid valve and which communicates with said discharge line;
- whereby rinse liquid from said rinsing tank is pumpable through said second rinse solenoid valve and through said first fitting into said second basin, and liquid in said second basin is discharged through said second fitting and through said circulation solenoid valve into said discharge line and through said discharge solenoid valve into said discharge tank.

13. A unit according to claim 12, wherein:
- a first T connector has a first leg thereof connected to said rinse tank, a second leg of said first T connector being connected to said first rinse solenoid valve, and a third leg of said first T connector being connected to said second rinse solenoid valve;
- a second T connector has a first leg thereof connected to said discharge tank, a second leg of said second T connector being connected to said first discharge solenoid valve, and a third leg of said second T connector being connected to said second discharge solenoid valve;
- third, fourth, and fifth T connectors, said third T connector having a first leg connected to said first pump, a second leg of said second T connector being connected to said fourth T connector, and a third leg of said second T connector being connected to said fifth T connector;
- said fourth T connector having a first leg connected to said third T connector, a second leg of said fourth T connector being connected to said first circulation solenoid valve, and a third leg of said fourth T connector being connected to said first rinse solenoid valve;
- said fifth T connector having a first leg connected to said third T connector, a second leg of said fifth T connector being connected to said first treatment solenoid valve, and a third leg of said fifth T connector being connected to said first discharge solenoid valve.

14. A method of treating electrophoretic strips mounted on a frame, said method comprising the steps of:
(1) pumping a treatment liquid from a first treatment liquid tank through a first liquid treatment draw line and through a first pump to a first basin wherein an electrophoretic strip is mounted on a frame, said first pump being in fluidic communication with said first treatment liquid draw tank through said first liquid treatment draw line as well as to a discharge tank through a discharge line and to a rinse tank through a rinse draw line;
(2) opening a treatment liquid valve on said first liquid treatment draw line while closing a rinse valve on said rinse draw line and closing a discharge valve on said discharge line as said treatment liquid is pumped from said first treatment liquid tank to said first basin;
(3) pumping liquid from said first basin through said first pump and through said discharge line;
(4) opening said discharge valve on said discharge line while closing said treatment liquid valve on said first liquid treatment draw line and closing said rinse valve on said rinse draw line and as said liquid is pumped from said first basin to said discharge tank;
(5) pumping a rinsing liquid from said rinse tank through rinse draw line and through said first pump to said first basin;
(6) opening a rinse valve on said rinse draw line while closing a first treatment valve on said first treatment draw line and closing a discharge valve on said discharge line as said rinsing liquid is pumped from said rinse tank to said first basin;
(7) closing said rinse valve and opening a circulation valve, said circulation valve communicating a conduit from said first basin with said first pump whereby liquid is circulated from said first basin through said first pump and back into said first basin; and,
(8) repeating steps (3) and (4).

15. The method of claim 14, further comprising:
sensing a maximum liquid level in said first basin and stopping the pumping of a liquid into said first basin upon the sensing of said maxium liquid level; and,
sensing a minimum liquid level in said first basin and stopping the pumping of a liquid from said first basin upon the sensing of said minimum liquid level.

16. The method of claim 14, further comprising:
communicating said first basin with said discharge basin for discharging any overflow liquid from said first basin.

17. The method of claim 14, further comprising:
(9) pumping a treatment liquid from a second treatment liquid tank through a second liquid treatment draw line and through a second pump to a second basin wherein an electrophoretic strip is mounted on a frame, said second pump being in fluidic communication with said second treatment liquid draw tank through said second liquid treatment draw line as well as to said discharge tank through said discharge line and to said rinse tank through said rinse draw line;
(10) opening a treatment liquid valve on said second liquid treatment draw line while closing a rinse valve on said rinse draw line and closing a discharge valve on said discharge line as said treatment liquid is pumped from said second treatment liquid tank to said second basin;
(11) pumping liquid from said second basin through said second pump and though said discharge line;
(12) opening said discharge valve on said discharge line while closing said treatment liquid valve on said second liquid treatment draw line and closing said rinse valve on said rinse draw line and as said liquid is pumped from said second basin to said discharge tank;
(13) pumping a rinsing liquid from said rinse tank through rinse draw line and through said second pump to said second basin;
(14) opening a rinse valve on said rinse draw line while closing a second treatment valve on said second treatment draw line and closing a discharge valve on said discharge line as said rinsing liquid is pumped from said rinse tank to said second basin;
(15) closing said rinse valve and opening a circulation valve, said circulation valve communicating a conduit from said second basin with said second pump whereby liquid is circulated from said second basin through said second pump and back into said second basin; and,
(16) repeating steps (11) and (12).

18. The method of claim 17, further comprising:
sensing a maximum liquid level in said second basin and stopping the pumping of a liquid level in said second basin and stopping the pumping of a liquid into said second basin upon the sensing of said maximum liquid level; and,
sensing a minimum liquid level in said second basin and stopping the pumping of a liquid from said second basin upon the sensing of said minimum liquid level.

19. The method of claim 17, further comprising;
communicating said second basin with said discharge basin for discharging any overflow liquid from said second basin.

* * * * *